US00PP10879P

United States Patent [19]

Bergman

[11] Patent Number: Plant 10,879

[45] Date of Patent: May 4, 1999

[54] HIBISCUS PLANT NAMED 'SAHARA WIND'

[75] Inventor: Wendy R. Bergman, Lehigh Acres, Fla.

[73] Assignee: Yoder Brothers, Inc., Barberton, Ohio

[21] Appl. No.: 08/995,356

[22] Filed: Dec. 29, 1997

[51] Int. Cl.[6] ..... A01H 5/00

[52] U.S. Cl. ..... Plt./67.8

[58] Field of Search ..... Plt./67.8

*Primary Examiner*—Elizabeth Kemmerer

*Attorney, Agent, or Firm*—C. A. Whealy

[57] ABSTRACT

A new and distinct cultivar of Hibiscus plant named 'Sahara Wind', characterized by its large dark green leaves; upright and outwardly spreading, uniform and symmetrical plant habit that is appropriate for container production; floriferousness with numerous large light orange-colored flowers with red throats; good resistance to flower bud abscission; and excellent postproduction longevity.

1 Drawing Sheet

The present invention relates to a new and distinct cultivar of Hibiscus, botanically known as *Hibiscus rosa-sinensis*, and hereinafter referred to by the cultivar name Sahara Wind.

The new cultivar is a product of a planned breeding program conducted by the inventor in Alva, Fla. The objective of the breeding program is to create new Hibiscus cultivars having uniform and compact plant habits appropriate for container production, early and uniform flowering, numerous flowers per lateral branch, desirable flower color, resistance to flower bud abscission, and good postproduction longevity.

The new cultivar originated from a cross made by the inventor in Alva, Fla., of a proprietary *Hibiscus rosa-sinensis* selection, designated as code number 511, as the female, or seed, parent with the *Hibiscus rosa-sinensis* cultivar Waikiki (disclosed in U.S. Plant Pat. No. 7,834) as the male, or pollen, parent. The cultivar Sahara Wind was discovered and selected by the inventor as a flowering plant within the progeny of the stated cross in a controlled environment in Alva, Fla., on Jul. 13, 1994.

Compared to plants of the female parent, the proprietary Hibiscus selection code number 511, plants of the new Hibiscus have lighter green and larger leaves, more outwardly spreading plant habit, and larger flowers. Plants of the new Hibiscus differ in flower color, have a more outwardly spreading plant habit, and flower about one week earlier than plants of the male parent, the cultivar Waikiki.

Asexual reproduction of the new cultivar by terminal cuttings taken in a controlled environment in Alva, Fla., has shown that the unique features of this new Hibiscus are stable and reproduced true to type in successive generations.

The cultivar Sahara Wind has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Sahara Wind'. These characteristics in combination distinguish 'Sahara Wind' as a new and distinct cultivar:

1. Large dark green leaves.
2. Upright and outwardly spreading, uniform and symmetrical plant habit that is appropriate for container production.
3. Very freely flowering, numerous large light orange-colored flowers with red throats.
4. Good resistance to flower bud abscission.
5. Excellent postproduction longevity.

Plants of the new Hibiscus can be compared to plants of the nonpatented cultivar Sundance. However, in side-by-side comparisons conducted in Alva, Fla., plants of the new cultivar differ from plants of the cultivar Sundance in the following characteristics:

1. Plants of the new Hibiscus are more compact than plants of the cultivar Sundance.
2. Plants of the new Hibiscus are more freely branching than plants of the cultivar Sundance.
3. Plants of the new Hibiscus flower about one week earlier than plants of the cultivar Sundance.

BRIEF DESCRIPTION OF THE PHOTOGRAPHS

The accompanying colored photographs illustrate the overall appearance of the new cultivar, showing the colors as true as it is reasonably possible to obtain in colored freproductions of this type.

The photograph at the top of the sheet comprises a top perspective view of typical plant of 'Sahara Wind'.

The photograph at the bottom of the sheet comprises a close-up view of a typical flower of 'Sahara Wind'. Flower and foliage colors in the photographs may appear different from the actual colors due to light reflectance.

DETAILED BOTANICAL DESCRIPTION

The following observations, measurements and values describe plants grown in Alva, Fla., and Keller, Tex., in 28-cm containers during the summer and early autumn with day temperatures ranging from 16 to 35° C. and night temperatures ranging from 10 to 24° C. In the description, color references are made to The Royal Horticultural Society Colour Chart except where general terms of ordinary dictionary significance are used.

Botanical classification: *Hibiscus rosa-sinensis* cultivar Sahara Wind.

Parentage:

*Female or seed parent.*—*Hibiscus rosa-sinensis* proprietary selection designated as code number 511.

*Male or pollen parent.*—*Hibiscus rosa-sinensis* cultivar Waikiki, disclosed in U.S. Plant Pat. No. 7,834.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright to outwardly spreading, inverted triangle, uniform and symmetrical plant habit. Moderate vigor.

*Branching habit.*—Freely branching, usually four to five lateral branches develop after removal of terminal apex.

*Plant height, soil level to top of flowers.*—About 40 cm.

*Plant diameter, area of spread.*—About 47 cm.

*Lateral branch description.*—Length: About 35 cm. Diameter: About 9 mm. Texture: Immature, smooth; woody with age.

*Color.*—Immature: Close to 144A. Mature: Grayish brown.

Foliage description:

*Arrangement.*—Alternate, single.

*Length.*—About 11 cm.

*Width.*—About 8.25 cm.

*Shape.*—Mostly ovate, cordate.

*Apex.*—Acute to acuminate.

*Base.*—Obtuse to cordate.

*Margin.*—Crenate.

*Texture.*—Glabrous and glossy/shiny on both surfaces.

*Color.*—Young foliage, upper surface: Brighter and darker than 146A. Young foliage, lower surface: Brighter and greener than 146A. Mature foliage, upper surface: Dark green, darker than 147A. Mature foliage, lower surface: Slightly lighter than 147A.

*Petiole.*—Length: About 3.75 cm. Diameter: About 3 mm. Texture: Smooth or with very fine pubescence on upper surface. Color: Upper, 147A; lower, close to 144A.

Flower description:

*Natural flowering season.*—Usually spring and summer or during periods of warm weather.

*Flower arrangement.*—Flowers arranged singly at terminal leaf axils. Very freely flowering with usually about five flower buds and/or open flowers per terminal apex. Flowers flat and face upright.

*Flower appearance.*—Large star-shaped single. Light orange-colored petals with red throat. Flowers are open for about one day before closing. Flowers self-cleaning.

*Flower diameter.*—About 12.5 cm.

*Flower bud (just before showing color).*—Rate of opening: About one day depending on temperatures. Length: About 2.5 cm. Diameter: About 1.3 cm. Shape: Columnar, oblong.

*Petals.*—Texture: Crepe, ruffled. Arrangement: Corolla consists of five petals that overlap. Shape: Spatulate with rounded apex. Margin: Entire, slightly ruffled. Length: About 7.5 cm. Width: About 5 cm. Color: Upper surface: 24A to 23A, 51A at base. Lower surface: 25B to 23B. Throat: Red, 46A, shiny.

*Sepals.*—Appearance: Six sepals fused into a star-shaped calyx. Shape: Linear. Texture: Smooth. Color, outer surface: 146A.

*Peduncles.*—Length: About 4 cm. Diameter: About 2.5 mm at apex. Angle: Upright. Strength: Strong, rigid. Color: 146A.

*Reproductive organs.*—Androecium: Stamen number: Numerous. Stamen length: About 5 mm. Anther shape: Globular. Anther size: About 1 mm. Amount of pollen: Abundant. Pollen color: 21A. Gynoecium: Pistil length: About 7.75 cm. Style color: Apex: 51B/51C. Base: 46A. Stigma number: Five. Stigma shape: Round. Stigma diameter: About 1.5 mm. Stigma color: 46A. Ovary color: Light green, 154C.

Disease resistance: No known Hibiscus diseases observed to date on plants grown under commercial greenhouse conditions.

Seed production: If cross-pollinated, seed production may be observed. Usually one to twenty seeds per capsule.

It is claimed:

1. A new and distinct Hibiscus plant named 'Sahara Wind', as illustrated and described.

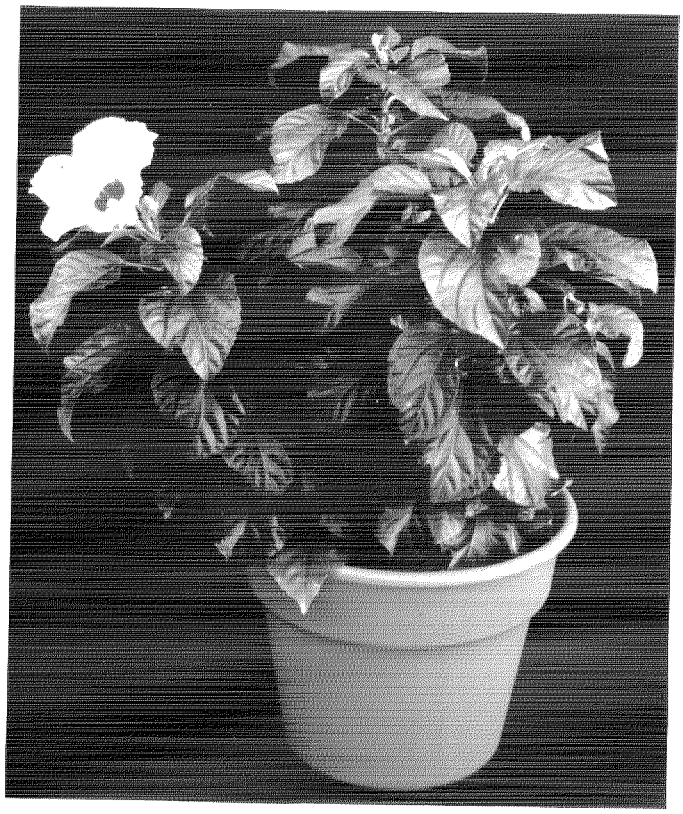
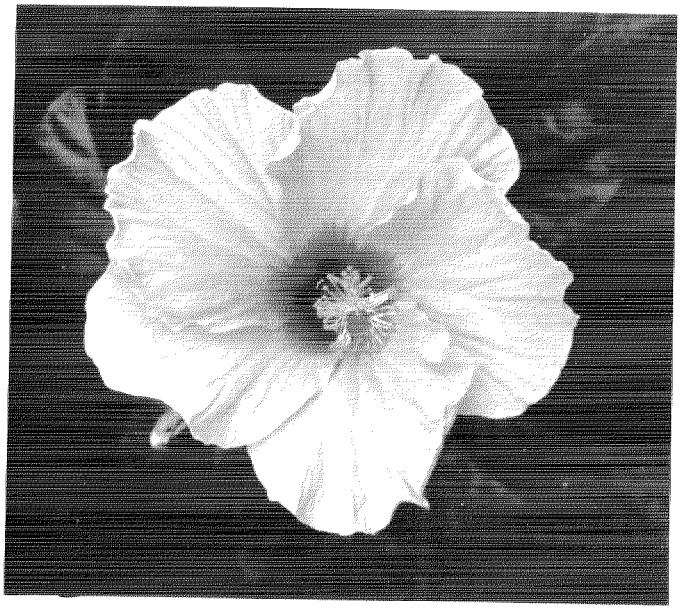

* * * * *